United States Patent [19]
Laszczower

[11] 4,435,170
[45] Mar. 6, 1984

[54] ASSEMBLY FOR RECEIVING AND DISCHARGING A COLLECTION OF BLOOD

[75] Inventor: Max Laszczower, Basel, Switzerland

[73] Assignee: Solco Basel AG, Switzerland

[21] Appl. No.: 273,711

[22] Filed: Jun. 15, 1981

[51] Int. Cl.³ .................. A61M 37/00; A61B 19/00
[52] U.S. Cl. ............................................ 604/4; 604/5;
604/403
[58] Field of Search ..................... 137/205; 141/8, 18;
128/276, 278, 214 R, 297; 251/6; 604/4, 5, 9,
27, 28, 30, 33, 34, 35, 403, 44

[56] References Cited
U.S. PATENT DOCUMENTS

| 2,309,302 | 1/1943 | Butler et al. | 251/6 |
| 3,191,600 | 6/1965 | Everett | 128/214 R |
| 3,896,733 | 7/1975 | Rosenberg | 128/214 R |
| 3,951,145 | 4/1976 | Smith | 128/272 |
| 4,047,526 | 9/1977 | Reynolds et al. | 604/4 |
| 4,065,093 | 12/1977 | Phillips | 251/6 |

Primary Examiner—C. Fred Rosenbaum
Assistant Examiner—J. L. Kruter
Attorney, Agent, or Firm—Neil F. Markva

[57] ABSTRACT

The assembly comprises a blood collection vessel, a flexible tube removably connected to the collection vessel and a flow control mechanism for regulating the flow of liquid into or out of the collection vessel. One of the shaped sections of the collection vessel has a size effective to be grasped by the hand of an operator. Inlet and outlet means are disposed at opposite ends of the vessel so that blood may be introduced into the vessel at one end and discharged at the other end when desiring to place the blood back into the person. Other specific features of the invention include the particular structural configuration of the flow control mechanism the disposition of a flexible tube between the flow control mechanism and the collection vessel and other features of the collection vessel.

20 Claims, 7 Drawing Figures

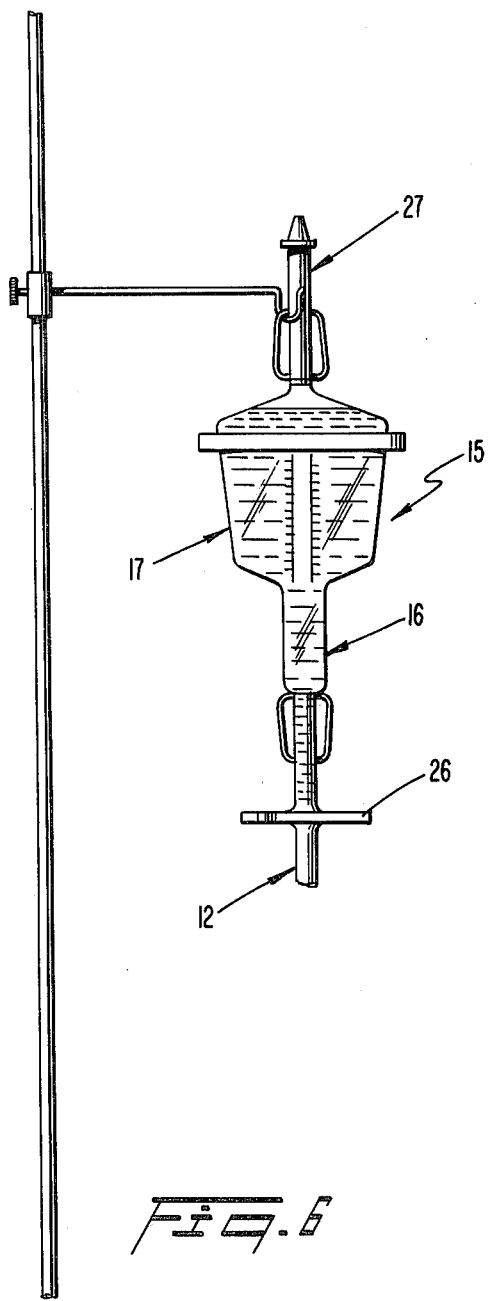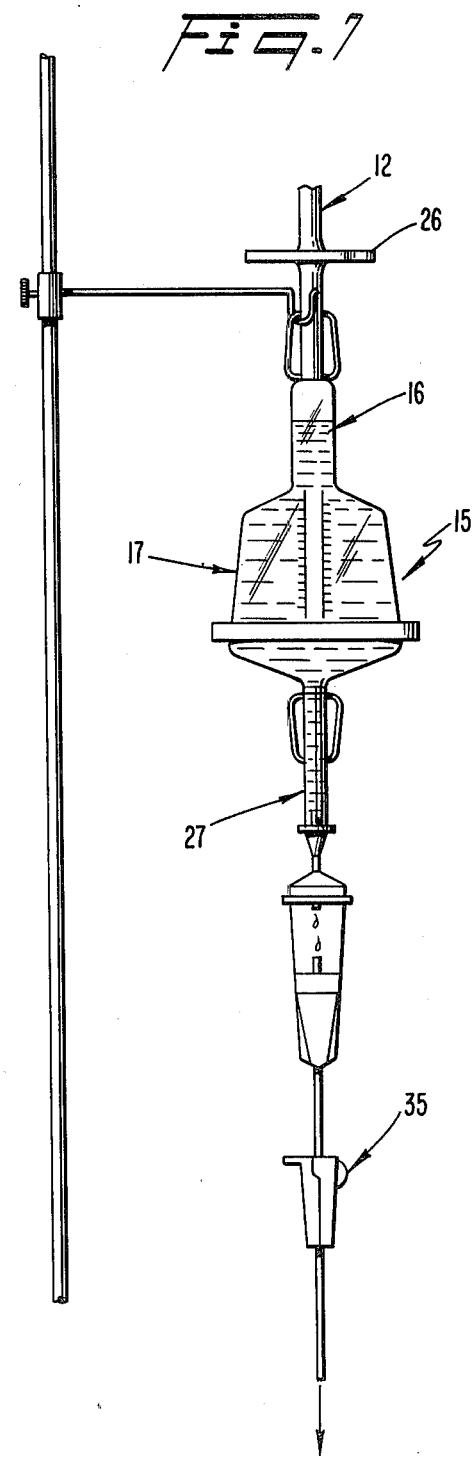

ASSEMBLY FOR RECEIVING AND DISCHARGING A COLLECTION OF BLOOD

FIELD OF THE INVENTION

The invention relates to an auto-transfusion apparatus and method. More particularly, the invention relates to a combination of a flow regulating device and a collection vessel.

BACKGROUND OF THE INVENTION

There are many situations in which considerable quantities of blood accumulate in a human body cavity. This blood must be sucked from the patient's body cavities and collected in a container of a suitable type and later has to be reintroduced into the patient's body.

Extreme care has to be taken during a transfusion process. This includes avoiding the coagulation of the blood and reducing the dissolution of red blood cells, known as hemolysis, to a minimum.

It is known to transfer blood by a roller pump from a patient to a suitable container. A first hose connects the roller pump and the container while a second hose connected to the container is used to carry the blood back into the circulatory system of the patient. Each one of these prior art hoses measures approximately two meters. During use, blood is sucked from the body cavity during an operation and collected in the container.

Before the blood is sucked, whole system has to be filled with a salt solution which acts as an anti-coagulating medium. During reinfusion of the blood, the anti-coagulating medium is introduced into the patient's body along with the blood.

There are several disadvantages associated with this known system and procedure. (1) The roller pump and the blood reservoir are located at a stationary location far removed from the operating table. (2) The corresponding flexible tubes between the sucking end and the container is at least 82 centimeters in length. (3) Any blood is likely to coagulate while travelling along these long hoses. Therefore, large amounts of anti-coagulating additives are added to prevent the coagulation of the blood. (4) The roller pump has a tendency to injure the delicate red blood cells when passing therethrough. Consequently, the content of free hemoglobin in the plasma is increased. (5) The delicate conditions and disposition of the various parts of the known systems requires specialized persons to operate the prior art devices. (6) Because of the configuration of the prior art systems, the risk of air embolism is significant. (7) Because of the large overall size of the known system, more than one person is generally required to operate the apparatus.

The known systems also include additional tubular element connected to the flexible tubing for containing anti-coagulating medium. This additional tubular element is required to avoid blood coagulation in the long flexible hose used with the prior art system. Consequently, the known system is extremely large and bulky.

PURPOSE OF THE INVENTION

The primary object of the invention is to avoid the disadvantages of the prior art systems by providing an apparatus for the auto-transfusion of blood without causing any injury to the red blood cells while preventing coagulation of the blood.

Another object of the invention is to provide a system having a transfusion apparatus with an overall size permitting complete operation by only one person.

Another object of the invention is to provide an assembly for receiving and discharging a collection of blood while regulating the flow of blood through a flexible hose connected to a collection vessel.

A still further object of the invention is to provide a collection vessel having a special structural configuration which will enable the blood to be collected during the initial sucking operation, mixed with a coagulating fluid, stored the required amount of time and then provide a blood source during reinfusion of the blood into the patient's body.

SUMMARY OF THE INVENTION

The assembly as described herein comprises a collection vessel having inlet and outlet means disposed at opposite ends thereof. A flexible tube is connected to at least one of the inlet or outlet means. Flow control means are removably disposed on the flexible tube at a location spaced from the collection vessel. The flow control means includes a coupling means rigidly mounted at one end of a support element and handle means disposed at the other end of the element. The flexible tube is removably connected to one end of the coupling means while the other end of the coupling means includes an opening for directing liquid therethrough into or out of said flexible tubing.

A particular feature of the invention is directed to the structural configuration of the collection vessel. The vessel comprises a first shaped section located at one end thereof and a second shaped section located at the other end thereof. First and second shaped sections are in fluid communication with respect to each other. One of the shaped sections has a size effective to be grasped by the hand of an operator. Inlet and outlet openings are disposed at opposite ends of the vessel and include openings in each of the first and second shaped sections. Indicia extend from the first and second shaped sections to measure the amount of fluid within the shaped sections when either one of the is disposed in a downward direction. Filter means is disposed at a location within the vessel between the inlet and outlet means. The first shaped section has a volume smaller than the volume of the second shaped section. The outer size and shape of the first shaped section is effective to be grasped by the hand of an operator.

The inlet and outlet means includes means for coupling a tube to either one of the openings located in the first and second shaped sections.

Another feature of the invention is directed to the particular structure of the flow control mechanism which has a tube coupling means rigidly mounted at one end of a support element and a handle means disposed at the other end of the element. A first end of the coupling means has a structural configuration effective for connecting a flexible tube and a second end of the coupling means has an opening that is in open communication with the first end thereof. Hand manipulatable means is mounted on the support element for regulating the flow of fluid through a flexible tube when a flexible tube is connected to the first end of the coupling means. The second end of the coupling means has a structural configuration effective to be connected to a rigid tube section which may have a suction head at the other end thereof. The handle means has a structural configuration effective to be grasped by the palm of an operator's hand while allowing the freedom of the thumb of the operator's hand to manipulate the fluid flow regulating means.

In a specific embodiment of the flow control device, the fluid flow regulating means includes a pair of walls upwardly extending from the support element at a location between the handle means and the coupling means. Roller means movably mounted with respect to the pair of walls is effective to control the amount of fluid flowing in a flexible hose disposed between the roller means and the support element. Each of the walls includes an inclined slot while the roller means includes axles disposed within the guide slots to move therein. The roller means includes a roller having an outer circumferential surface effective to be in depressing contact with respect to a flexible hose disposed between the roller and the support element.

A further feature of the invention is directed to the method of operating the assembly disclosed and described herein. A suction head is located on one end of the tube removably connected to the coupling means of a flow control apparatus. The suction head is inserted into a pool of anti-coagulation liquid which is sucked into the collection vessel until a first shaped section thereof is filled with the desired mount of the anti-coagulation liquid. The suction head is then inserted into the body cavity containing the blood which is sucked into the collection vessel while the flow through the flexible tubing is regulated with the flow control means. Once the blood has been removed from the cavity, the vacuum is terminated, the flexible hose clamped and cut. To reinfuse the blood into the patient's body, the collection vessel is inverted and the blood reintroduced through the other end of the collection vessel after having passed through the filter means disposed within the collection vessel.

BRIEF DESCRIPTION OF DRAWINGS

Other objects of this invention will appear in the following description and appended claims, reference being made to the accompanying drawings forming a part of the specification wherein like reference characters designate corresponding parts in the several views.

FIG. 4 is a sectional view of an embodiment of a rigid tube section used with the blood handling assembly of the invention;

FIG. 5 is an elevational view of a collection vessel made in accordance with this invention;

FIG. 6 is an elevational view of the collection vessel of FIG. 5 as it is shown in a blood storing function; and FIG. 7 is an elevational view of a blood handling assembly of the invention being used to reinfuse blood into a patient.

DETAILED DESCRIPTION

Figure 1:
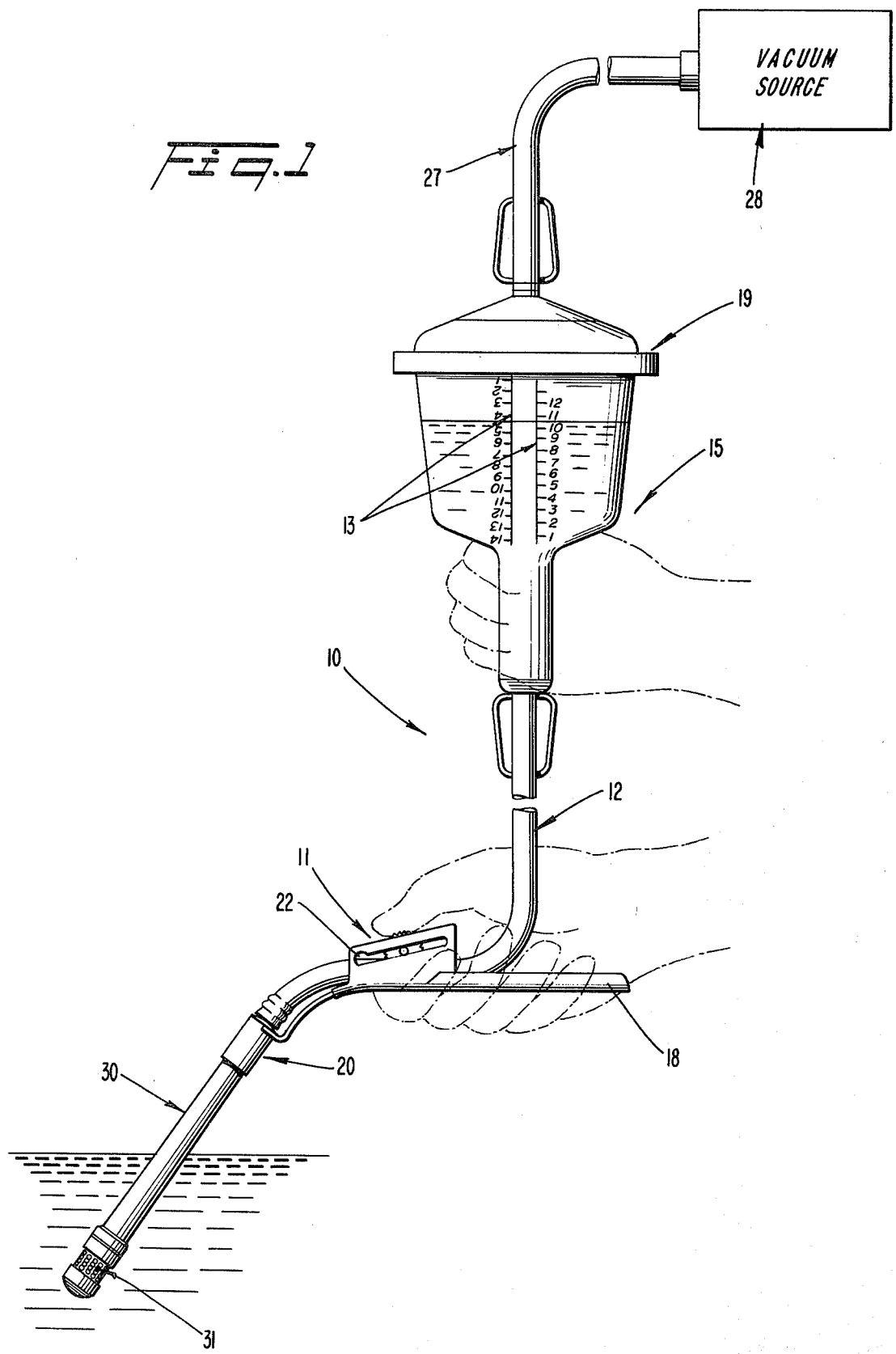
FIG. 1 is a perspective view of a blood handling assembly made in accordance with the invention.
Figure 2:
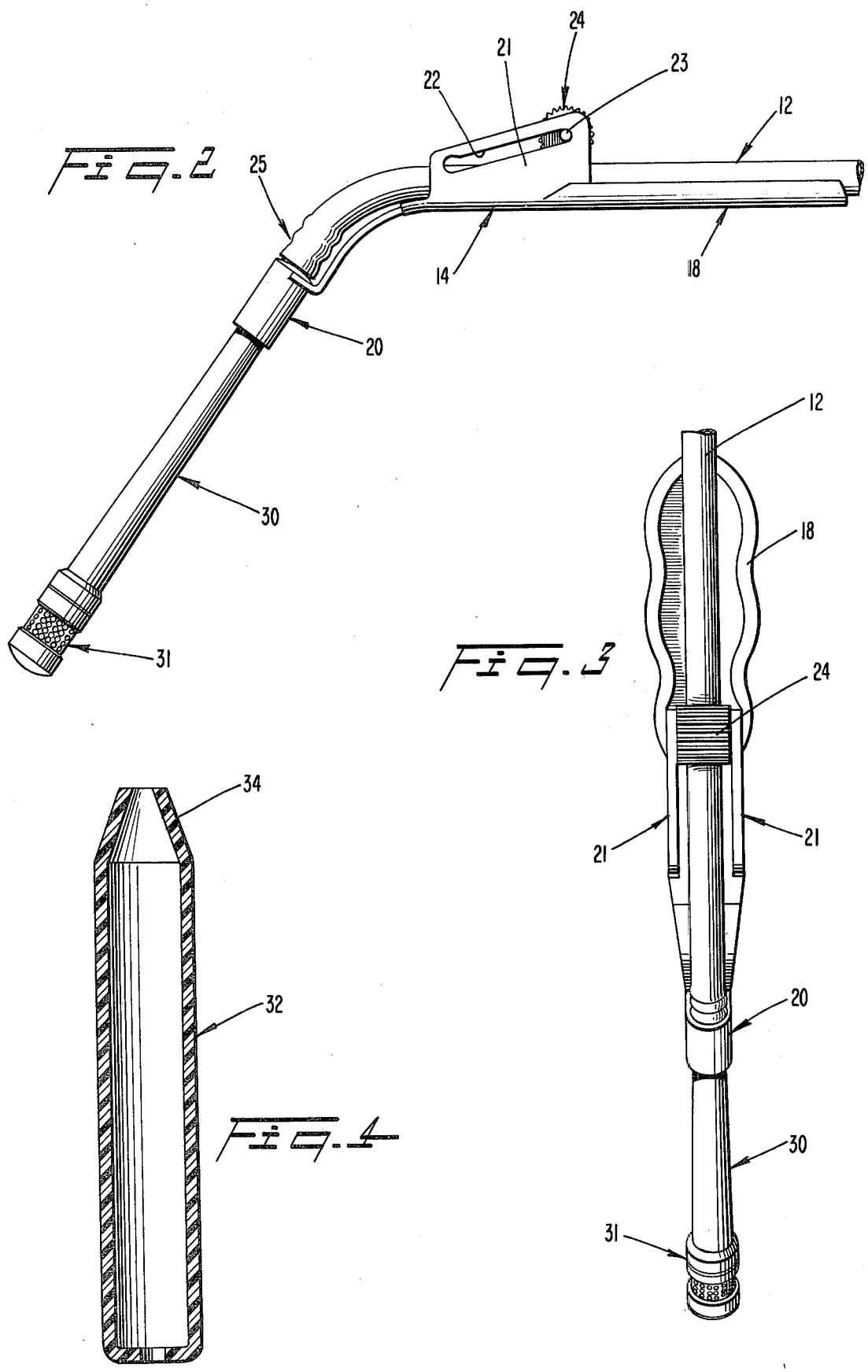
FIG. 2 is an elevational view of a control mechanism made in accordance with the invention.
Figure 3:
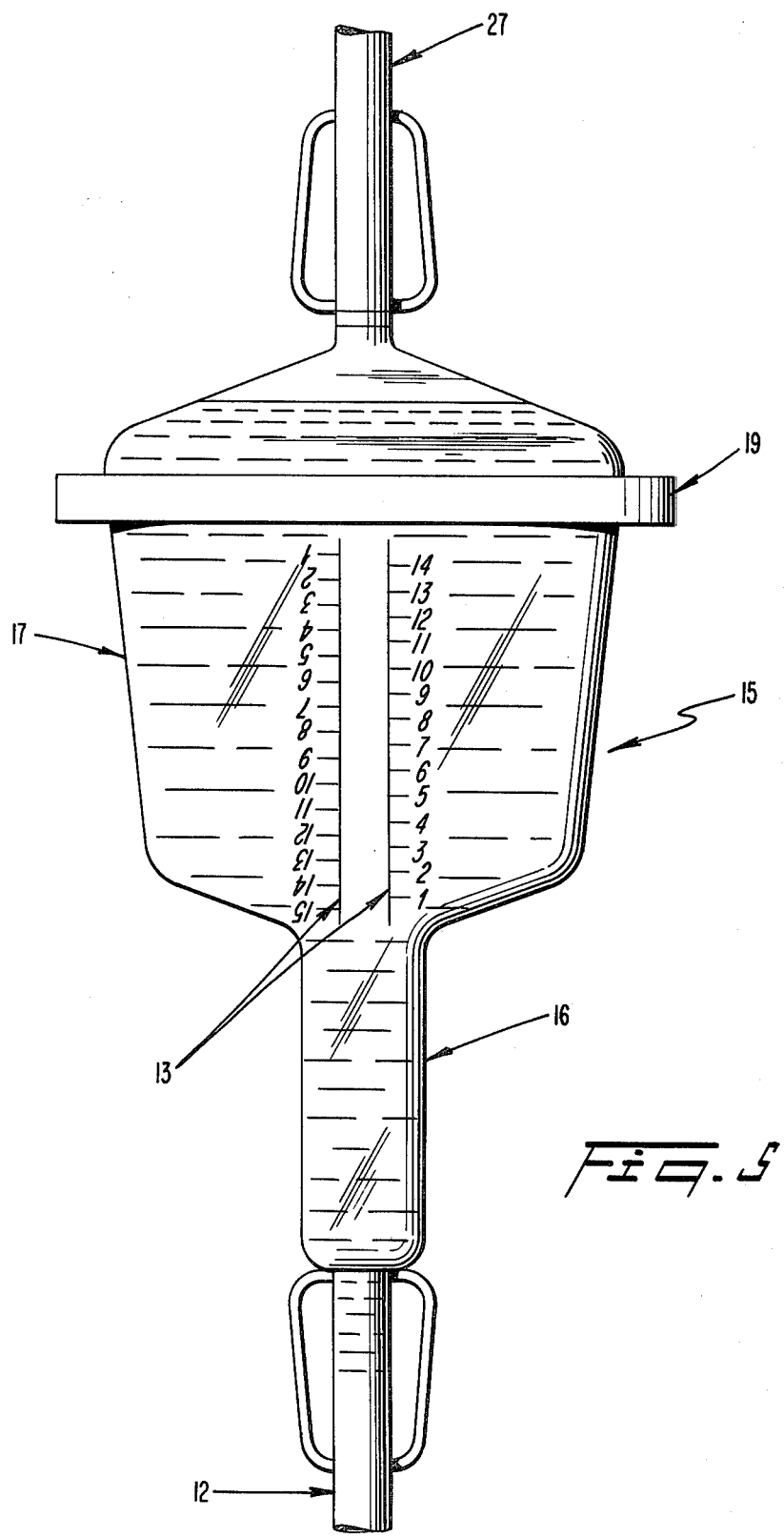
FIG. 3 is a front elevational view of the mechanism shown in FIG. 2.

The blood handling assembly, generally designated 10, includes a collection vessel 15, a flow control mechanism 11 and a flexible tube 12. Vessel 15 includes a first shaped section 16 that is in fluid communication with a second shaped section 17. The shaped section 16 has a size effective to be grasped by the hand of an operator. The inlet opening is located in shaped section 16 and is shown connected to the hose 12 in FIG. 1. Indicia 13 extend along the first and section shaped sections 16 and 17 to measure the amount of fluid within the vessel 15 when either one of the shaped sections 16 and 17 is disposed in a downward direction. A filter pad 19 is treated with an anti-foaming agent and positioned within the vessel 15 as shown.

As shown in FIG. 1, a flow control mechanism, generally designated 11, is disposed on the hose 12. Flow control mechanism 11 includes a support element 14 having a handle 18 at one end thereof and a coupling mechanism 20 at the other end thereof. A fluid flow regulating means includes a pair of walls 21 upwardly extending from the support element 14 and including an inclined guide slot 22. A roller 24 is positioned between the side walls 21 and carries an axle 23 which is supported at either end within the guide slot 22.

The handle 18 has a structural configuration effective to be grasped in the palm of the user so that the thumb is free to operate the roller 24 which moves upwardly and downwardly within the guide slot 22 with respect to the support element 14. When the flexible tube 12 is disposed on support element 14, the roller 24 has an outer circumferential surface effective to be in depressing contact with respect to the flexible hose 12. Thus, it is possible to control the flow of liquid along the length of the flexible tube 12.

The coupling mechanism 20 includes a tube connection 25 at one end thereof where the flexible tube is removably connected. A rigid tube section 30 is connected to the other end of the coupling mechanism 20. When connected to the second end of coupling mechanism 20, the rigid tube 30 is used as a suction tube during the suction of blood from the body cavity. The end of the rigid suction tube is conically shaped and the second connection of coupling mechanism 20 has a conical cavity corresponding to the shape of the suction tube 30. The connection is effective as a frictional connection.

The rigid tube section 30 includes a suction head 31 which includes a plurality of orifices around the periphery thereof. During the suction process, suction head 31 has to be fully immersed in the blood pool of the patient's body cavity. Suction head 31 must be fully immersed so that no air is sucked through the rigid tube section 30 because any air would cause foaming of the blood causing an extremely dangerous situation as far as the reinfusion procedure is concerned. Foaming of the blood will cause death.

As shown in FIG. 1, the vessel 15 is connected at its outlet end to a vacuum source 28 via a flexible tube 27. Once the suction procedure is complete, a clamp 26 is placed across the tube 12 which is then subsequently cut. Vessel 15 is then readied for the reinfusion procedure by inserting a drip flow regulating device 35 to the outlet or discharge end of vessel 15. Once connected, the vessel 15 is inverted and the reinfusion process is then begun such as is shown in FIG. 7. Until the reinfusion process is required, the collection vessel 15 may be suspended in the manner shown in FIG. 6 where it can be stored until the time that reinfusion is to be initiated.

Another embodiment of a rigid suction tube is shown in FIG. 4 which may be used instead of the rigid tube section 30. The conical end of this embodiment would fit into the conical cavity of the coupling mechanism 20 rigidly attached to the end of the support element 14.

The overall assembly has numerous advantages over the prior art transfusion devices. The flexible tube 12 has a link sufficient to enable the collecting vessel 15 to be in close proximity to the flow regulating device 11 when tube 12 is in a taut condition. In this specific embodiment, the length of flexible tube 12 is about 40 centimeters. The shorter length of suction tube 30 enables the operator to use the whole system as disclosed in combination in chose proximity to the patient. This represents a significant number of advantages over the prior art structures which are deemed to be readily apparent.

A coupling mechanism or element 20 interrupts any motion between the flexible tube 12 and the rigid tube 30. Thus, regardless of pressure applied, any motion created on flexible tube 12 is interrupted by the rigidly disposed coupling element 20. Unwanted movement of the suction tube 30 and the head 31 is thereby eliminated. An operator can easily position the suction head 31 at a precise location in the body cavity containing blood. In other words, the flow control device 11 clearly provides a much greater degree of control when compared to any similar devices in the prior art.

A preliminary procedure should be used in those instances where anti-coagulating material is to help in controlling the flow conditions within the blood. In such an instance, suction head 31 is immersed in a container containing anti-coagulating liquid. Thus, anti-coagulating liquid is drawn into the first shaped section 16 in a measured fashion. Thus, the first shaped section 16 acts as a measuring device. Once the anti-coagulating liquid has reached the desired level as determined on the measuring indicia 13, the suction head 31 is immersed into the body cavity containing the blood. Any blood sucked into the vessel 15 is then necessarily mixed with the anti-coagulating liquid. Any known anti-coagulating liquid may be used such as sodium citrate.

The assembly of the present invention is compact, easily operable, and may be used for all of the operations required in removing blood from an open body cavity, storing same for a period of time and then reinfusing the blood back to the patient after filtering. The unique design of the flow control mechanism 11 enables the operator to handle a short length of flexible tube 12 while maintaining a firm grasp onto the design collection vessel 15. Thus, one person is able to operate the system in close proximity to the patient thereby eliminating many of the disadvantages associated with the known prior art devices.

While the assembly for receiving and discharging a collection of blood has been shown and described in detail, it is obvious that this invention is not to be considered as being limited to the exact form disclosed, and that changes in detail and construction may be made therein within the scope of the invention, without departing from the spirit thereof.

Having thus set forth and disclosed the nature of this invention, what is claimed is:

1. An assembly operable by a single person for receiving by aspiration, storing and discharging a collection of blood to the same patient, said assembly comprising:
   (a) a single vessel means for collection and dispensing having a structural configuration effective to be held in one hand of an operator and further effective for receiving and storing blood, said vessel means having a plurality of chamber means for alternate collection and dispensing of the aspirated blood and having inlet and outlet means disposed at opposite ends thereof, one of said chamber means having a lesser diameter than the other chamber means,
   (b) a flexible tube removably connected to one of the inlet or outlet means,
   (c) fluid flow aspirating regulating means removably disposed on the said flexible tube at a location spaced from said collection vessel means, said flow regulating means including coupling means rigidly mounted to one end of a support element means to support the flexible tube and handle means disposed at the other end of said element means, said handle means having a structural configuration effective to be held simultaneously in the other hand of the operator while said lesser diameter chamber means of the vessel means is being held in said one hand of the operator while the flow of blood is simultaneously regulated by the fluid flow regulating means,
   (d) said flexible tube being removably connected to one end of said coupling means and the other end of said coupling means including an opening for directing liquid therethrough into and out of said flexible tubing,
   (e) said fluid flow regulating means including a pair of walls upwardly extending from the support element at a location between the handle means and the coupling means, roller means movably mounted with respect to the pair of walls and being effective to control the amount of fluid flowing in a flexible hose disposed between said roller and the support element.

2. An apparatus as defined in claim 1 wherein said vessel comprises a first shaped section located at one end thereof and a second shaped section located at the other end thereof, said first and second shaped sections being in fluid communication with respect to each other, one of said shaped sections having a size effective to be grasped by the hand of an operator, inlet and outlet openings being disposed at opposite ends of said vessel and including openings in each of said first and second shaped section, and indicia extending from said first and second shaped sections to measure the amount of fluid within said shaped sections when either one of said shaped sections is disposed in a downward direction.

3. An apparatus as defined in claim 1 wherein filter means is disposed at a location within said vessel between the inlet and outlet means thereof.

4. An apparatus as defined in claim 1 wherein said first shaped section has a volume smaller than the volume of said second shaped section, the outer size of said first shaped section being effective to be grasped by the hand of an operator.

5. An assembly as defined in claim 1 wherein said inlet and outlet means includes means for coupling a tube to either one of said openings located in the first and second shaped sections.

6. An apparatus as defined in claim 1 wherein said second end of the coupling means has a structural configuration effective to be connected to a tube section.

7. An apparatus as defined in claim 1 wherein a rigid tube section is connected at said second end of the coupling means and has a suction head at the other end thereof.

8. An assembly as defined in claim 1 wherein said handle means has a structural configuration effective to be grasped by the palm of an operator's hand while allowing the freedom of the thumb of the operator's hand to manipulate said fluid flow regulating means.

9. An apparatus as defined in claim 1 wherein indicia extends along said first and second shaped sections to measure the amount of fluid within said shaped sections when either one of said shaped sections is disposed in a downward direction.

10. An assembly as defined in claim 1 wherein said flexible tube has a length effective to enable the collection vessel to remain in near proximity of the flow controlling means when said flexible tube is in a taut condition.

11. An assembly as defined in claim 10 wherein said length of the flexible tube is about 40 centimeters.

12. An assembly as defined in claim 10 wherein a tube section is removably connected to the second end of the coupling means and has a length smaller than the length of the flexible tube.

13. An assembly operable by a single person for receiving by aspiration, storing and discharging a collection of blood for autotransfusion purposes to the same patient, said assembly comprising:
   (a) a single vessel means for collection and dispensing flexible inlet tube means, rigid suction tube means, vacuum tube means and a liquid flow aspirating control clamp,
   (b) said vessel means having two chamber means for alternate collection and dispensing of the aspirated blood with one of the chamber means of the collection vessel means being removably connected to one end of the flexible inlet tube means for receiving blood through said flexible inlet tube means,
   (c) the vacuum tube means being adapted to removably connect said collection vessel means to a vacuum source at the other chamber means of said vessel means remote from said chamber means connected to the inlet tube means,
   (d) one of the chamber means of said collection vessel means having a lesser diameter than the other chamber means enabling an operator to grasp said lesser diameter chamber means by one hand,
   (e) said flexible inlet tube means carrying the rigid suction tube means at its outer end opposite to said one end connected to said chamber means connected thereto and further carrying the liquid flow aspirating control clamp adjacent to said rigid suction tube means,
   (f) said flow aspirating control clamp being adapted to be connected to said suction tube means and having a handle to be grasped by the operator's other hand at a location spaced from the lesser diameter chamber of the collection vessel means, and
   (g) said flexible inlet tube means having a length effective to enable the collection vessel means to remain in near proximity of the suction tube means while the lesser diameter chamber means of the vessel means is held in one hand of the operator and the handle of the flow aspirating control clamp is simultaneously grasped by the operator's other hand so that the flow of blood is simultaneously controlled by the manipulation of the flow aspirating control clamp.

14. An assembly as defined in claim 13 wherein said length of said flexible inlet tube means is about 40 centimeters.

15. An assembly as defined in either claim 13 or 14 wherein said rigid suction tube means has a smaller length than that of the flexible inlet tube means.

16. An assembly as defined in any one of the claims 13, 14 or 15 wherein
   said rigid suction tube means has a suction head at the opposite end of its connection to the flexible tube means and,
   said suction head includes a plurality of orifices around the periphery thereof.

17. An assembly as defined in claim 13 wherein
   said handle has a structural configuration effective to be grasped by the palm of an operator's hand while allowing the freedom of the thumb of the operator's hand to manipulate said flow controlling clamp.

18. An assembly as defined in claim 13 wherein
   said collection vessel has a first shaped section with a smaller volume than that of a second shaped section,
   said flexible inlet tube means being connected to said first shaped section, and
   the outer size of said first shaped section being effective to be grasped by the operator's hand.

19. An assembly as defined in claim 18 wherein the collection vessel carries indicia extending along said first and second shaped sections to measure the amount of fluid within said shaped sections when either one of said shaped sections is disposed in a downward direction.

20. A method of operating the assembly of claim 13 for collecting and reinfusing blood, said method comprising:
   (a) inserting the suction head into a pool of anti-coagulation liquid,
   (b) creating vacuum conditions within said collection vessel until said first shaped section is filled with a desired amount of anti-coagulation liquid,
   (c) removing the suction head from the pool of anti-coagulation liquid and inserting said suction head into the body cavity containing blood,
   (d) sucking the blood and regulating the flow of the blood during the suction process,
   (e) terminating the vacuum conditions,
   (f) clamping the flexible tube means to stop the flow of blood,
   (g) cutting the flexible tube means and inverting the collection vessel, and
   (h) reinfusing blood discharging through the other end of said collection vessel after having passed through a filter means disposed within said collection vessel.

* * * * *